US012518616B2

(12) United States Patent
Terai et al.

(10) Patent No.: US 12,518,616 B2
(45) Date of Patent: Jan. 6, 2026

(54) PHYSIOLOGICAL ALARM CONTROL SYSTEM AND METHOD

(71) Applicant: NIHON KOHDEN CORPORATION, Tokyo (JP)

(72) Inventors: Kumi Terai, Tokorozawa (JP); Yuta Sekiguchi, Tokorozawa (JP); Daisuke Shimizu, Tokorozawa (JP); Tomoko Oku, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 33 days.

(21) Appl. No.: 18/633,645

(22) Filed: Apr. 12, 2024

(65) Prior Publication Data

US 2024/0355192 A1 Oct. 24, 2024

(30) Foreign Application Priority Data

Apr. 21, 2023 (JP) ................................ 2023-069941

(51) Int. Cl.
*G08B 29/18* (2006.01)
*A61B 5/00* (2006.01)
*G08B 21/04* (2006.01)

(52) U.S. Cl.
CPC ............ *G08B 29/185* (2013.01); *A61B 5/746* (2013.01); *G08B 21/0453* (2013.01)

(58) Field of Classification Search
CPC ......................... G08B 29/185; G08B 21/0453; G08B 21/182; A61B 5/318; A61B 5/746
See application file for complete search history.

(56) References Cited

U.S. PATENT DOCUMENTS

| | | | | |
|---|---|---|---|---|
| 8,269,634 B2 * | 9/2012 | Fischell | A61B 5/0031 | 607/30 |
| 8,570,167 B2 * | 10/2013 | Al-Ali | A61B 5/0816 | 600/323 |
| 8,648,723 B2 * | 2/2014 | Osone | A61B 5/002 | 600/300 |
| 9,095,316 B2 * | 8/2015 | Welch | A61B 5/14551 | |
| 10,565,850 B2 * | 2/2020 | Schlichting | G08B 29/12 | |
| 11,291,414 B2 * | 4/2022 | Koyama | A61B 5/746 | |
| 12,135,213 B1 * | 11/2024 | Grundy | G01C 21/16 | |
| 12,142,132 B1 * | 11/2024 | Ibarra | G08B 29/04 | |
| 2007/0055164 A1 * | 3/2007 | Huang | B60K 28/02 | 340/576 |
| 2016/0093205 A1 | 3/2016 | Boyer | | |

* cited by examiner

*Primary Examiner* — John A Tweel, Jr.
(74) *Attorney, Agent, or Firm* — McDonald Hopkins LLC

(57) ABSTRACT

An alarm control system includes an obtaining unit configured to obtain a message signal related to measurement of physiological information and an output value of the physiological information, a first alarm signal generator configured to generate a first alarm signal based on the message signal related to the measurement, a second alarm signal generator configured to generate a second alarm signal based on at least one of the message signal related to the measurement or a period in which a measurement value is invalid, the period being calculated based on the output value of the physiological information, and an output controller configured to perform control to output the first alarm signal and the second alarm signal.

21 Claims, 14 Drawing Sheets

(CONT.)

(FIG. 11 CONTINUED)
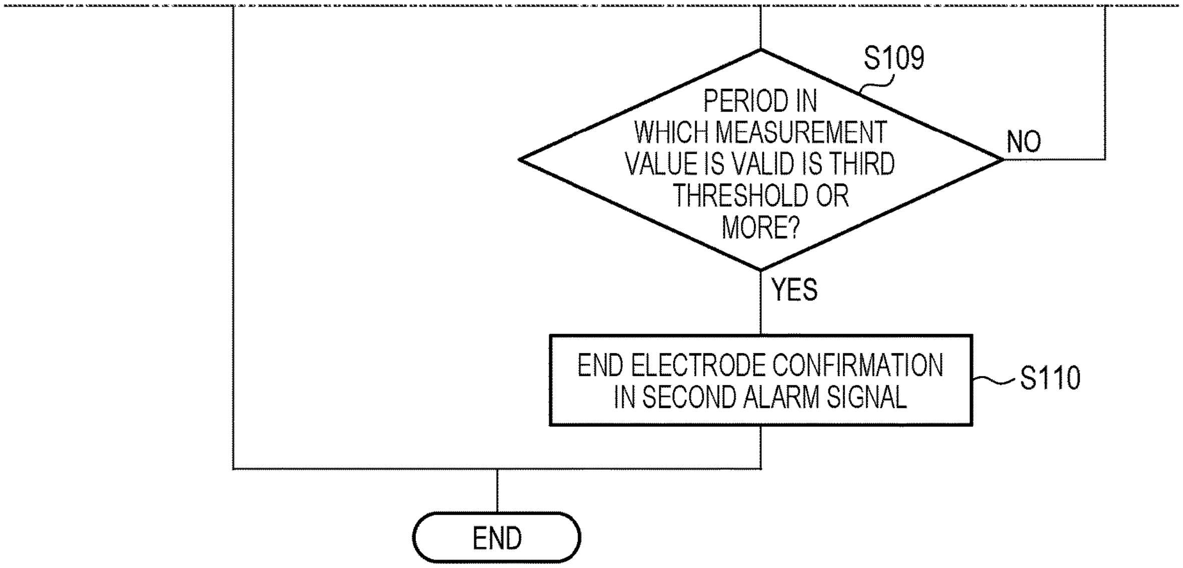

PHYSIOLOGICAL ALARM CONTROL SYSTEM AND METHOD

CROSS-REFERENCE TO RELATED APPLICATIONS

The present application claims the benefit of priority of Japanese Patent Application No. 2023-069941, filed on Apr. 21, 2023, the content of which is incorporated herein by reference.

TECHNICAL FIELD

The presently disclosed subject matter relates to an alarm control system, an alarm control method, and a non-transitory computer-readable storage medium storing an alarm control program.

BACKGROUND ART

In a patient monitor that displays the physiological information of a patient or the like, there has been a technique of outputting a physiological alarm (vital alarm) that notifies an abnormality detected in the physiological information or a device alarm (technical alarm) that notifies an abnormality related to the state of a medical device or a system that measures the physiological information.

When an alarm is notified, the medical staff or the like checks and deals with the contents of the alarm. For example, when a physiological alarm is notified, the state of the patient or the like is checked. When a sensor attached to the patient or the like is detached and a device alarm is notified, the sensor is attached to the patient or the like again.

However, as the number of sensors or medical devices attached to the patient or the like increases, the number of types and the number of times of the alarms to be notified increase, and the alarms may fatigue the medical staff or the like and may be ignored without being handled.

On the other hand, the notified alarms include a considerable number of alarms that do not need to be handled by the medical staff. For example, some alarms are caused by a noise due to a motion of the patient or the like being superimposed on a detection signal of a sensor. These alarms are naturally eliminated while the medical staff or the like is to take measures.

As a known technique for reducing such an alarm that does not need to be handled, there has been an alarm delay process of masking an alarm for a predetermined time from the occurrence of the alarm.

US2016/0093205A1 discloses the following prior art. Receive data related to a plurality of alarms generated in response to physiological parameters of each patient satisfying an alarm condition. Generate a plurality of validity indicators indicating the validity for a plurality of valid alarms based on information on the alarms input by the user. Analyze the data related to the plurality of alarms and the plurality of validity indicators. Then, correct at least one alarm condition based on the analysis.

SUMMARY

However, in the alarm delay process described above, if relatively short-time alarms occur frequently, it may be actually necessary for the medical staff or the like to confirm the patient or the like or adjust the sensor, but no alarms are notified.

Similarly, if relatively short-time alarms occur frequently, the prior art disclosed in US2016/0093205A1 cannot appropriately issue alarm notification while reducing the number of alarms that do not need to be handled. Further, the prior art disclosed in US2016/0093205A1 is also complicated because it is necessary for the user to input information on the valid alarms to correct the alarm condition.

The presently disclosed subject matter has been made to solve the above problems. That is, an object of the presently disclosed subject matter is to provide an alarm control system, an alarm control method, and an alarm control program capable of appropriately notifying alarms while reducing alarms that do not need to be handled.

The above problems of the presently disclosed subject matter are solved by the following means.

(1) An alarm control system including:

- an obtaining unit configured to obtain a message signal related to measurement of physiological information and an output value of the physiological information;
- a first alarm signal generator configured to generate a first alarm signal based on the message signal related to the measurement;
- a second alarm signal generator configured to generate a second alarm signal based on at least one of the message signal related to the measurement or a period in which a measurement value is invalid, the period being calculated based on the output value of the physiological information; and
- an output controller configured to perform control to output the first alarm signal and the second alarm signal.

(2) An alarm control method executed by an alarm control system, the alarm control method including:|

- obtaining a message signal related to measurement of physiological information and an output value of the physiological information;
- generating a first alarm signal based on the message signal related to the measurement;
- generating a second alarm signal based on at least one of the message signal related to the measurement or a period in which a measurement value is invalid, the period being calculated based on the output value of the physiological information; and
- performing control to output the first alarm signal and the second alarm signal.

(3) A non-transitory computer-readable storage medium storing an alarm control program for causing a computer to execute:

- obtaining a message signal related to measurement of physiological information and an output value of the physiological information;
- generating a first alarm signal based on the message signal related to the measurement;
- generating a second alarm signal based on at least one of the message signal related to the measurement or a period in which a measurement value is invalid, the period being calculated based on the output value of the physiological information; and
- performing control to output the first alarm signal and the second alarm signal.

The first alarm signal and the second alarm signal are output after generating the second alarm signal based on at least one of the first alarm signal generated based on the message signal related to the measurement of the physiological information or the period in which the measurement value of the physiological information is invalid calculated based on the output value of the physiological information.

Accordingly, alarms can be appropriately notified while reducing the number of alarms that do not need to be handled.

DESCRIPTION OF EMBODIMENTS

Figure 1:
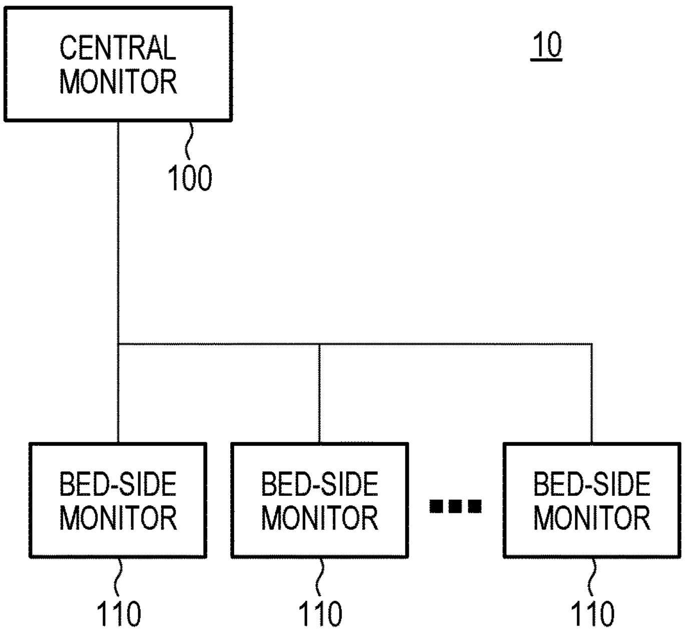
FIG. 1 is a schematic configuration diagram of a medical system.

Hereinafter, an alarm control system, an alarm control method, and an alarm control program according to an embodiment of the presently disclosed subject matter will be described in detail with reference to the drawings. In the drawings, the same elements are denoted by the same reference numerals, and the redundant description thereof is omitted.

(Medical System 10)

FIG. 1 is a schematic configuration diagram of a medical system 10. The medical system 10 may include a central monitor 100 and a bed-side monitor 110. One or more bed-side monitors 110 may be provided. Although the bed-side monitor 110 may include the sensor 114 (see FIG. 2), the sensor 114 may be configured as an apparatus separate from the bed-side monitor 110. For example, the sensor 114 may be configured with a transmitter capable of wirelessly communicating with the bed-side monitor 110.

The medical system 10 may include a centralized receiver communicably connected to the central monitor 100 and a plurality of transmitters wirelessly communicable with the centralized receiver. Some or all of the plurality of bed-side monitors 110 may be replaced by the centralized receiver and the plurality of transmitters.

The central monitor 100 and the bed-side monitors 110 are mutually and communicably connected via a wired or wireless network. Examples of the network include local area network (LAN) and wide area network (WAN). For example, Ethernet (registered trademark), Wi-Fi (registered trademark), Bluetooth (registered trademark), or 5G may be used as a communication standard of the network.

(Bed-Side Monitor 110)

Figure 2:
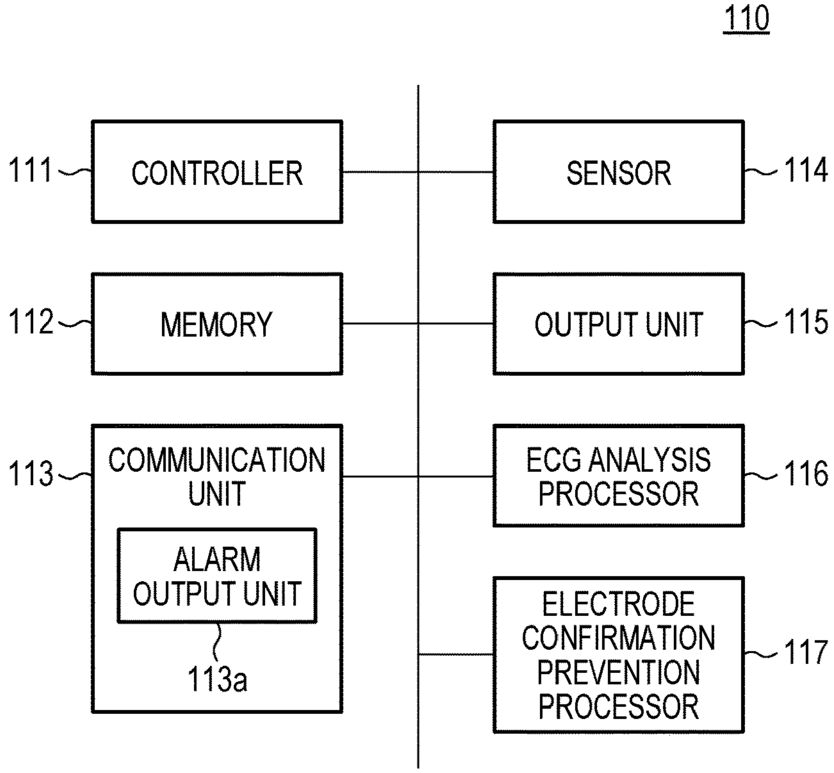
FIG. 2 is a block diagram of a hardware configuration of a bed-side monitor.

FIG. 2 is a block diagram of a hardware configuration of the bed-side monitor 110. The bed-side monitor 110 may include a controller 111, a memory 112, a communication unit 113, a sensor 114, an output unit 115, an ECG analysis processor 116, and an electrode confirmation prevention processor 117. These components are mutually connected via a bus. The ECG analysis processor 116 and the electrode confirmation prevention processor 117 may be configured as an apparatus separate from the bed-side monitor 110. In this case, the ECG analysis processor 116 and the electrode confirmation prevention processor 117 may be communicably connected to the bed-side monitor 110 via a network or the like. The ECG analysis processor 116 and the electrode confirmation prevention processor 117 may each include an arithmetic apparatus (computer). The bed-side monitor 110 is provided, for example, for each patient's bed or each patient's room. The controller 111 constitutes a switching unit.

The controller 111 may include, for example, a central processing unit (CPU) and a random access memory (RAM), controls the components of the corresponding bed-side monitor 110, and performs various calculations.

The controller 111 causes the communication unit 113 to transmit the physiological information detected by the sensor 114 to the central monitor 100 as a detection signal of the physiological information. The controller 111 detects an abnormality in the physiological information based on the physiological information, and if an abnormality is detected, transmits a signal of a physiological alarm (vital alarm) for notifying the abnormality in the physiological information together with the physiological information to the central monitor 100 via the communication unit 113. The physiological information may include, for example, an electrocardiogram (ECG), the heart rate (HR), the arterial blood oxygen saturation (SpO2), the blood pressure, the respiration (RESP), and carbon dioxide (CO2) of expiration and inhalation. The abnormality of the physiological information can be detected by, for example, exceeding an upper limit value, a lower limit value, or upper and lower limit values set for the physiological information.

The controller 111 transmits a device alarm (technical alarm) generated and output by the electrode confirmation prevention processor 117 to the central monitor 100 through the communication unit 113. As described later, the device alarm signal may include an electrode confirmation alarm signal (see FIG. 3). The abnormality notified by the device alarm may include, for example, an abnormality of an apparatus or the like including a measurement device (device or element) constituting the sensor 114, an abnormality of the attachment state such as detachment of the sensor 114 attached to the patient, and an abnormality of the measurement environment such as mixed noise. Specifically, examples of the device alarm may include "electrode confirmation" and "probe confirmation". "Electrode confirmation" is a device alarm related to the attachment of an electrode for measuring physiological information to the measurement subject (patient), and is an alarm occurring due to the detachment of an electrode lead from an ECG electrode attached to the patient, the floating of the ECG electrode from the body, the disconnection of the electrode lead, or the like. "Probe confirmation" is an alarm occurring due to the disconnection/short circuit or the like of a probe attached to the patient for measuring or transmitting the physiological information, such that the probe is detached from the body, or the probe is detached from a relay cord or a measurement device. Hereinafter, in order to simplify the description, a case where the device alarm is "electrode confirmation" will be described as an example. The signal for notifying the device alarm of "electrode confirmation" transmitted to the central monitor 100 is referred to as an "electrode confirmation alarm signal".

The controller 111 may associate identification information for identifying the subject (patient or the like) of the physiological information with identification information for identifying the type of the alarm, and transmit the physiological information and the alarms to the central monitor 100 together with the identification information. The identification information for identifying the subject of the physiological information may include, for example, the bed number of the patient, the ID of the patient, and the IP address of the bed-side monitor 110. The identification information for identifying the type of alarm may include, for example, information indicating a device alarm of "electrode confirmation", information indicating a physiological alarm of "heart rate", and information indicating a physiological alarm of "irregular pulse".

The memory 112 may include, for example, an SSD (solid state drive), and stores various data and various programs.

The communication unit 113 is an interface for communicably connecting the bed-side monitor 110 and the central monitor 100. The communication unit 113 may include, for example, an input terminal, an antenna, and a front-end circuit. The communication unit 113 may include an alarm output unit 113*a*. The alarm output unit 113*a* transmits (outputs) the alarms together with the identification information to the central monitor 100. Specifically, the alarm output unit 113*a* transmits, for example, an electrode confirmation alarm signal to the central monitor 100 in association with identification information indicating a device alarm of "electrode confirmation".

The sensor 114 is a device or an element for detecting the physiological information. The sensor 114 may include, for example, ECG measurement electrodes, an SpO2 probe, a blood pressure sensor, a choroid sensor, a temperature sensor, a CO2 sensor, a gas sensor, a respiration sensor, a contact sensor, and other measurement sensors capable of detecting the physiological information. The sensor 114 may output the detection result of the physiological information as a detection signal of the physiological information.

The output unit 115 displays (outputs) the physiological information and the alarms in a visually recognizable manner. The output unit 115 may be configured with, for example, a liquid crystal display. The output unit 115 may include an amplifier and a speaker to output the alarms in an audibly recognizable manner. The output unit 115 may transmit (output) the physiological information and the alarms as data to another apparatus. The output unit 115 may be configured with a printer to output the physiological information and the alarms by forming an image on a sheet.

Figure 3:
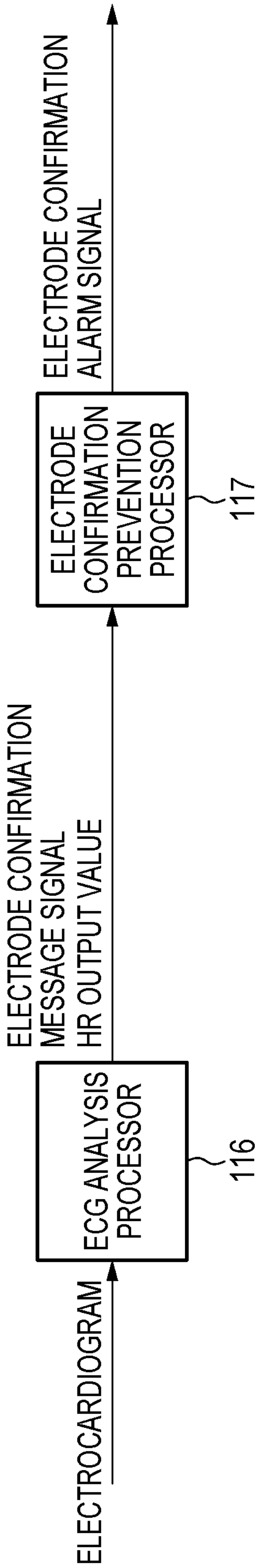
FIG. 3 is a block diagram for explaining the functions of an ECG analysis processor and an electrode confirmation prevention processor.

FIG. 3 is a block diagram for explaining the functions of the ECG analysis processor 116 and the electrode confirmation prevention processor 117.

The ECG analysis processor 116 receives a detection signal of the physiological information detected by the sensor 114 and analyzes the received detection signal to calculate a message signal related to the measurement of the physiological information and an output value of the physiological information. The detection signal of the physiological information may include, for example, an electrocardiogram (detection signal of an electrocardiogram). The message signal related to the measurement of the physiological information is a message signal that is a digital signal indicating whether a device alarm has occurred. Specifically, a message signal related to the measurement of the physiological information may include, for example, an electrode confirmation message signal indicating whether "electrode confirmation" has occurred. The electrode confirmation message signal is an example of a sensor confirmation message signal related to the attachment of the sensor 114 to the subject. The sensor confirmation message signal may include an electrode confirmation message signal, a probe confirmation message, or the like. The output value of the physiological information is either a measurement value of the physiological information calculated from the detection signal detected by the sensor 114 or an invalid value of the physiological information (for example, a value indicating that the measurement (calculation) of the physiological information is impossible). Specifically, the output value of the physiological information may include, for example, an output value of the heart rate (hereinafter, referred to as an "HR output value"). The HR output value is either the measurement value of the heart rate or an invalid value of the heart rate. If the heart rate cannot be calculated from the electrocardiogram, the HR output value becomes an invalid value.

Hereinafter, in order to simplify the description, a case in which the detection signal of the physiological information is an electrocardiogram will be described as an example. In the described example, the message signal related to the measurement of the physiological information is an electrode confirmation message signal determined from the sensor signal of the electrocardiogram. In addition, in the described example, the output value of the physiological information is an HR output value calculated by analyzing an electrocardiogram.

The electrode confirmation in the electrode confirmation message signal is generated when the waveform is clipped in the electrocardiogram. The clipping may occur when the waveform of the electrocardiogram exceeds the input dynamic range of the electronic circuit of the ECG analysis processor 116. The measurement value of the heart rate in the HR output value is calculated by calculating the heart rate from the electrocardiogram. The method of calculating a heart rate from an electrocardiogram is publicly known, and thus the description thereof is omitted. The HR output value is set to an invalid value if the heart rate cannot be calculated due to the disturbance of the waveform of the electrocardiogram because, for example, a noise is superimposed on the waveform of the electrocardiogram, or if the heart rate cannot be calculated because no input signals of the electrocardiogram are output.

The processes in the ECG analysis processor 116 may be executed by a CPU (not illustrated) included in the ECG analysis processor 116. Some or all of the processes performed by the ECG analysis processor 116 may be executed by the controller 111.

The electrode confirmation prevention processor 117 generates and outputs an electrode confirmation alarm signal based on at least one of the electrode confirmation message signal or the HR output value. Hereinafter, the process of the electrode confirmation prevention processor 117 generating the electrode confirmation alarm signal based on at least one of the electrode confirmation message signal or the HR output value is referred to as "electrode confirmation prevention process". Specifically, the electrode confirmation prevention processor 117 generates the first alarm signal by performing alarm delay process on the electrode confirmation message signal. The electrode confirmation prevention processor 117 calculates the frequency of electrode confirmation based on the electrode confirmation message signal. The electrode confirmation prevention processor 117 calculates a period in which the measurement value of the heart rate is an invalid value (a period in which the measurement value of the physiological information is invalid, hereinafter referred to as the "period in which the measurement value is invalid") based on the HR output value. The period other than the period in which the measurement value is invalid is referred to as a period in which the measurement value is valid. The electrode confirmation prevention processor 117 generates the second alarm signal based on at least one of the frequency of electrode confirmation or the period in which the measurement value is invalid. Then, the electrode confirmation prevention processor 117 outputs the first alarm signal and the second alarm signal. The electrode confirmation prevention processor 117 may output an integrated alarm signal obtained by merging the first alarm signal and the second alarm signal as the electrode confirmation alarm signal. That is, the electrode confirmation prevention processor 117 may output the logical sum (OR) of the first alarm signal and the second alarm signal as the electrode confirmation alarm signal. The electrode confirmation prevention processor 117 may output the first alarm signal and the second alarm signal as electrode confirmation alarm signals in a distinguishable manner, for example, by associating the electrode confirmation alarm signals with the identification information. Hereinafter, in order to simplify the description, a case where the electrode confirmation alarm signal is an integrated alarm signal obtained by merging the first alarm signal and the second alarm signal will be described as an example.

Figure 4:
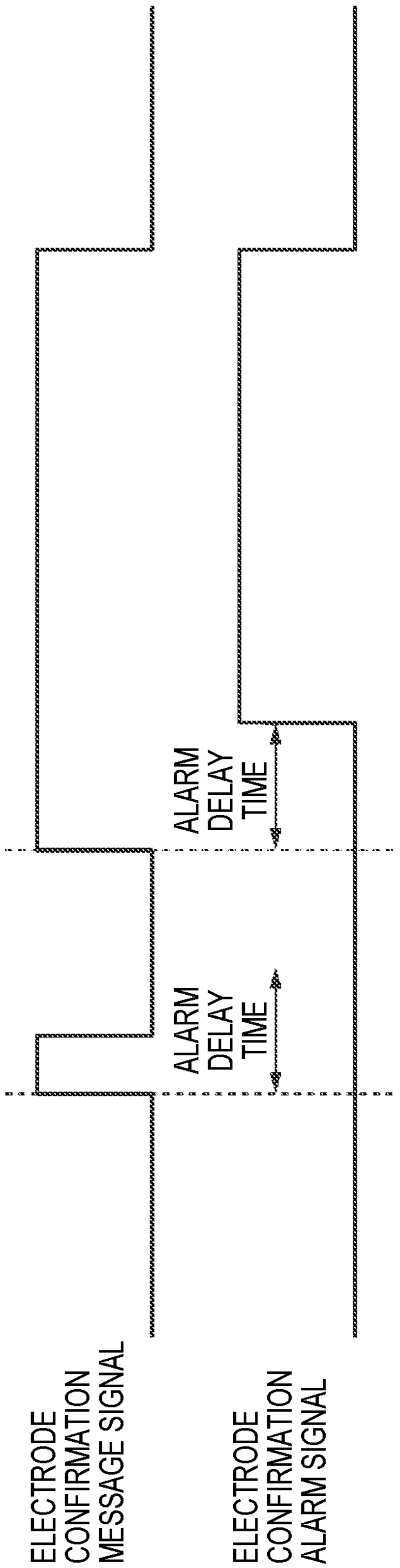
FIG. 4 is an explanatory diagram for explaining an alarm delay process.
Figure 5:
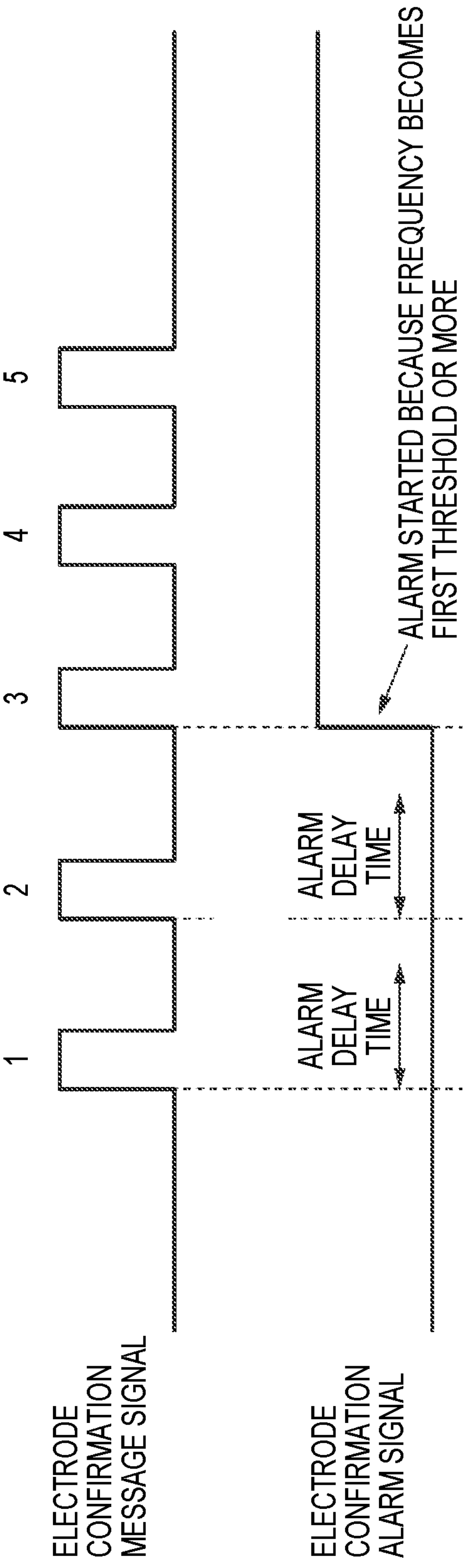
FIG. 5 is an explanatory diagram for explaining the start of an alarm in an electrode confirmation alarm signal based on the frequency of electrode confirmation.
Figure 6:
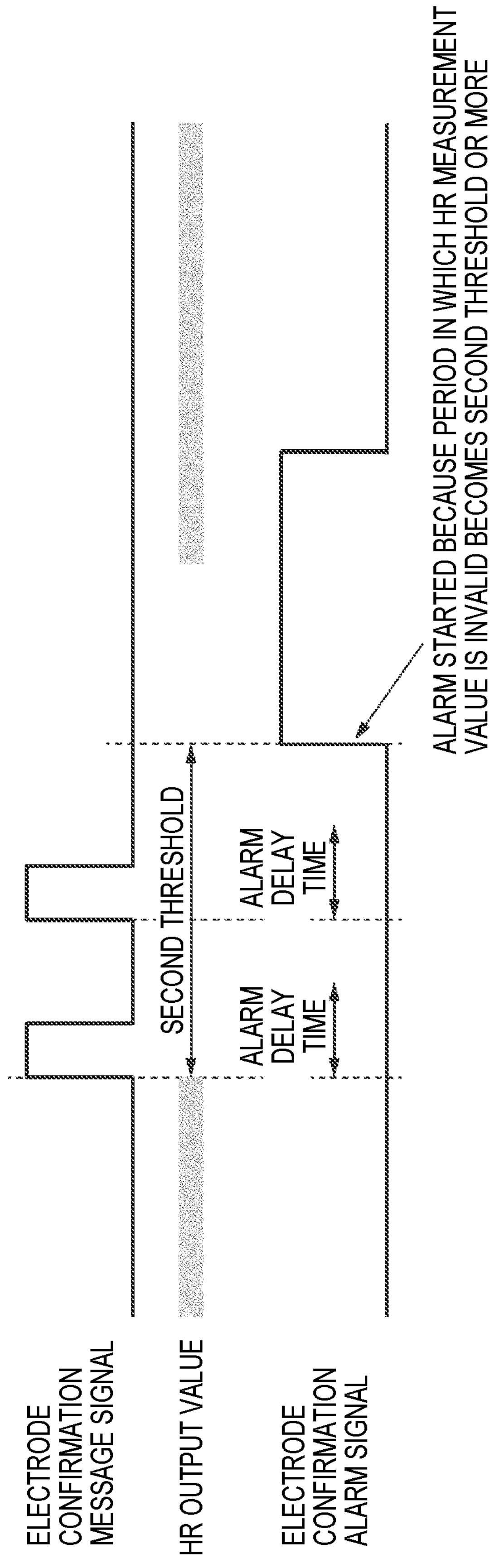
FIG. 6 is an explanatory diagram for explaining the start of the alarm in the electrode confirmation alarm signal based on the period in which a measurement value is invalid.
Figure 7:
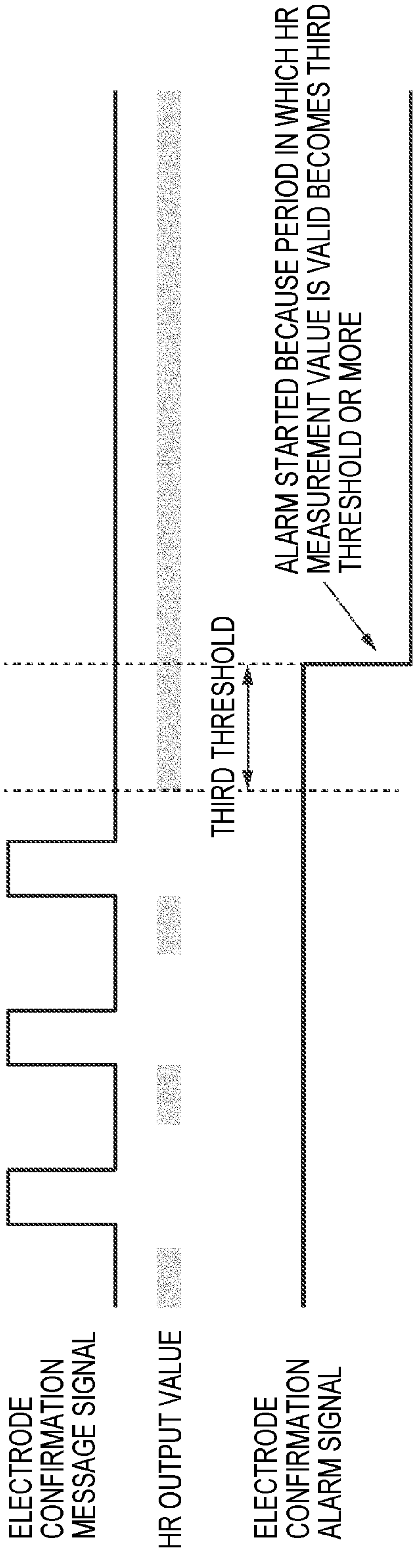
FIG. 7 is an explanatory diagram for explaining the end of the alarm in the electrode confirmation alarm signal based on the period in which the measurement value is valid.

FIG. 4 is an explanatory diagram for explaining the alarm delay process. FIG. 5 is an explanatory diagram for explaining the start of the alarm in the electrode confirmation alarm signal based on the frequency of electrode confirmation. FIG. 6 is an explanatory diagram for explaining the start of the alarm in the electrode confirmation alarm signal based on the period in which the measurement value is invalid. FIG. 7 is an explanatory diagram for explaining the end of the alarm in the electrode confirmation alarm signal based on the period in which the measurement value is valid.

Referring to FIG. 4, since the electrode confirmation message signal is subjected to an alarm delay process of masking the message for an alarm delay time (predetermined time) from the occurrence of electrode confirmation, the electrode confirmation of the predetermined time or less in the electrode confirmation message signal is erased in the electrode confirmation alarm signal. The alarm delay time may be set to an appropriate value through experiments or the like from the viewpoint of the alarm accuracy of electrode confirmation. The alarm delay time may be determined or changed depending on the type or state of the patient. For example, if the patient is severe, the alarm delay time may be set shorter to issue notification immediately. The alarm delay time may be determined or changed in consideration of the work load of the staff. For example, the alarm delay time may be changed between daytime and nighttime. The alarm delay time may be determined by the user in consideration of the use environment.

The alarm delay time may be determined by the following method based on the electrode confirmation alarm occurrence status and the response status thereof in the actually used environment or in a similar environment. For example, the alarm delay time may be determined such that the interruption of ECG monitoring due to electrode confirmation is the shortest as a result of: (1) data analysis; (2) machine learning including AI; (3) automatic learning; and (4) trial by an experimental method (trial and error, questionnaire, and the like).

The alarm delay time may be, for example, 5 seconds. Basically, relatively short-time electrode confirmation is highly probably device alarms that do not need to be handled. Therefore, the alarm delay process can prevent device alarms that do not need to be handled from being included in the electrode confirmation alarm signal.

Referring to FIG. 5, electrode confirmation is started in the electrode confirmation alarm signal when the frequency of electrode confirmation calculated based on the electrode confirmation message signal becomes a first threshold or more. The first threshold may be set to an appropriate value through experiments or the like from the viewpoint of the alarm accuracy of electrode confirmation. The first threshold may be determined or changed depending on the type or state of the patient. For example, if the patient is severe, the first threshold may be set smaller to issue notification immediately. The first threshold may be determined or changed in consideration of the work load of the staff. For example, the first threshold may be changed between daytime and nighttime. The first threshold may be determined by the user in consideration of the use environment.

The first threshold may be determined by the following method based on the electrode confirmation alarm occurrence status and the response status thereof in the actually used environment or in a similar environment. For example, the first threshold may be determined such that the interruption of ECG monitoring due to electrode confirmation is the shortest as a result of: (1) data analysis; (2) machine learning including AI; (3) automatic learning; and (4) trial by an experimental method (trial and error, questionnaire, and the like).

The frequency of electrode confirmation may be the cumulative number of continuous electrode confirmation if electrode confirmation continues occurring within 30 seconds or less after the end of the previously occurring electrode confirmation. In this case, the first threshold may be three times. The first threshold may be, for example, three times per 30 seconds. As described above, since the electrode confirmation alarm signal is an integrated alarm signal obtained by merging the first alarm signal and the second alarm signal, the result of the alarm delay process is reflected in the electrode confirmation alarm signal of FIG. 5. If the frequency of electrode confirmation is relatively increased due to frequent occurrence of relatively short-time electrode confirmation, such electrode confirmation is highly probably device alarms that need to be handled. However, the alarm delay process may erase relatively frequent and relatively short-time electrode confirmation. The electrode confirmation is started in the electrode confirmation alarm signal when the frequency of the electrode confirmation becomes the first threshold or more, thereby enabling more appropriate notification of device alarms of electrode confirmation.

In the HR output value of FIG. 6, a period indicated by gray color indicates the period in which the measurement value is valid (the same applies to FIG. 7). Referring to FIG. 6, electrode confirmation is started in the electrode confirmation alarm signal when the period in which the measurement value is invalid (the period other than the period indicated in gray color in which the measurement value is valid) determined based on the HR output value becomes a second threshold or more. The second threshold may be set to an appropriate value through experiments or the like from the viewpoint of the alarm accuracy of electrode confirmation. The second threshold may be determined or changed depending on the type or state of the patient. For example, if the patient is severe, the second threshold may be set smaller to issue notification immediately. The second threshold may be determined or changed in consideration of the work load of the staff. For example, the second threshold may be changed between daytime and nighttime. The second threshold may be determined by the user in consideration of the use environment.

The second threshold may be determined by the following method based on the electrode confirmation alarm occurrence status and the response status thereof in the actually used environment or in a similar environment. For example, the second threshold may be determined such that the interruption of ECG monitoring due to electrode confirmation is the shortest as a result of: (1) data analysis; (2) machine learning including AI; (3) automatic learning; and (4) trial by an experimental method (trial and error, questionnaire, and the like).

The second threshold may be, for example, 30 seconds. As described above, since the electrode confirmation alarm signal is an integrated alarm signal obtained by merging the first alarm signal and the second alarm signal, the result of the alarm delay process is reflected in the electrode confirmation alarm signal of FIG. 6. If the period in which the measurement value is invalid is relatively long, even if electrode confirmation does not occur in the electrode confirmation message signal, it is considered that the electrocardiogram is disordered to the extent that the heart rate cannot be calculated, which highly probably needs to be handled. Therefore, electrode confirmation is started in the electrode confirmation alarm signal if the period in which the measurement value is invalid becomes relatively long.

Referring to FIG. 7, the electrode confirmation is ended in the electrode confirmation alarm signal when the valid period other than the period in which the measurement value is invalid calculated based on the HR output value becomes the third threshold or more. The third threshold may be set to an appropriate value through experiments or the like from the viewpoint of the alarm accuracy of electrode confirmation. The third threshold may be determined or changed depending on the type or state of the patient. For example, if the patient is severe, the third threshold may be set larger to make it difficult to end the electrode confirmation. The third threshold may be determined or changed in consideration of the work load of the staff. For example, the third threshold may be changed between daytime and nighttime. The third threshold may be determined by the user in consideration of the use environment.

The third threshold may be determined by the following method based on the electrode confirmation alarm occurrence status and the response status thereof in the actually used environment or in a similar environment. For example, the third threshold may be determined such that the interruption of ECG monitoring due to electrode confirmation is an appropriate time as a result of: (1) data analysis; (2) machine learning including AI; (3) automatic learning; and (4) trial by an experimental method (trial and error, questionnaire, and the like). The third threshold may be, for example, 5 seconds. As described above, since the electrode confirmation alarm signal is an integrated alarm signal obtained by merging the first alarm signal and the second alarm signal, the result of the alarm delay process is reflected in the electrode confirmation alarm signal of FIG. 7. When the period in which the measurement value is valid becomes relatively long, it is considered that the electrocardiogram stops being disordered and has become stable, which highly probably does not need to be handled. Therefore, electrode confirmation is ended in the electrode confirmation alarm signal if the period in which the measurement value is valid becomes relatively long.

The electrode confirmation prevention process in the electrode confirmation prevention processor 117 may be executed by a CPU (not illustrated) included in the electrode confirmation prevention processor 117. A part or all of the electrode confirmation prevention process performed by the electrode confirmation prevention processor 117 may be performed by the controller 111. The electrode confirmation prevention processor 117 constitutes an obtaining unit, a first alarm signal generator, a calculation unit, a second alarm signal generator, and an output controller.

Figure 8:
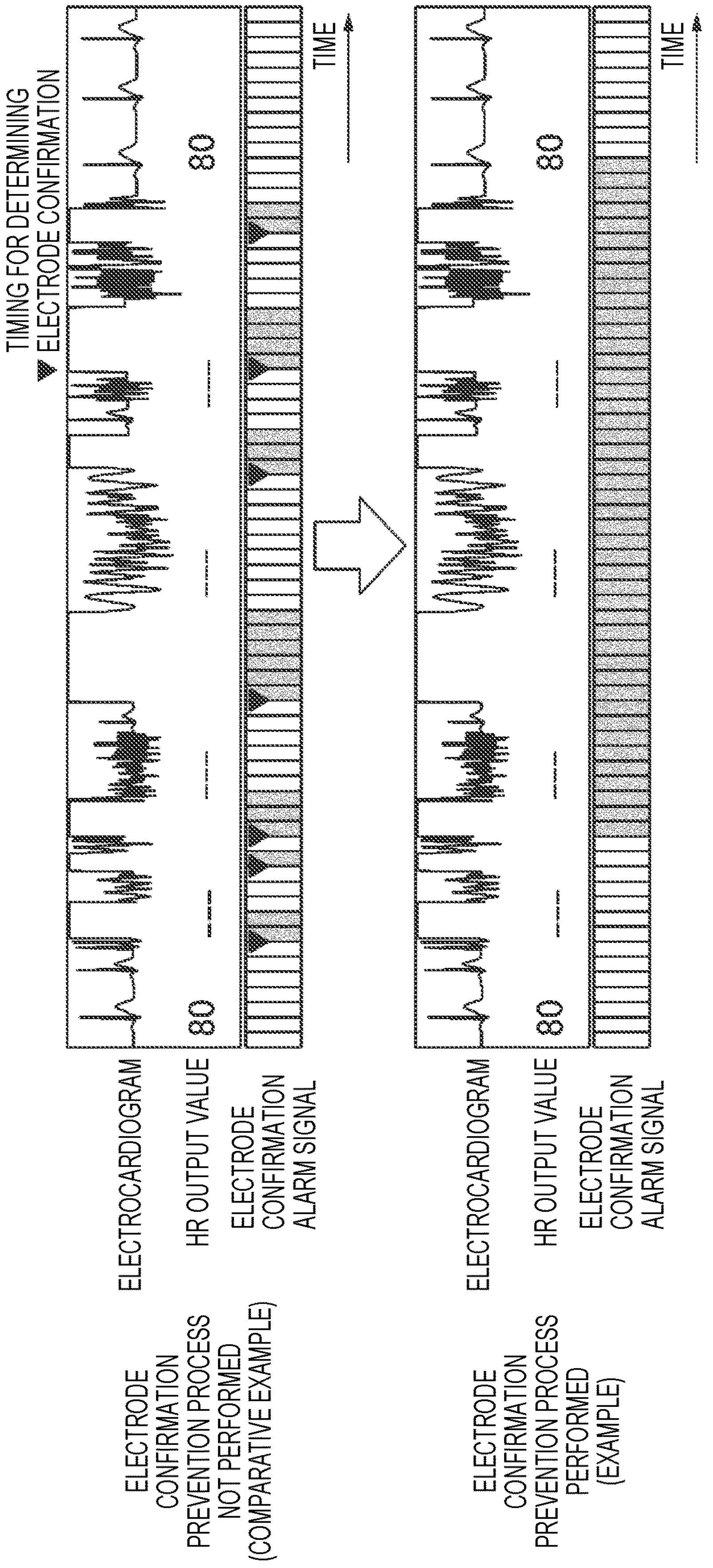
FIG. 8 is an explanatory diagram illustrating an electrocardiogram, an HR output value, and an electrode confirmation alarm signal when the electrode confirmation prevention process is performed, in comparison with a case where the electrode confirmation prevention process is not performed.

FIG. 8 is an explanatory diagram illustrating an electrocardiogram, an HR output value, and an electrode confirmation alarm signal when the electrode confirmation prevention process is performed, in comparison with a case where the electrode confirmation prevention process is not performed.

In the example of FIG. 8, in the HR output value, the measurement value of the heart rate is displayed as “80”, and the invalid value is displayed as “- - -”. In the electrode confirmation alarm signal, the period during which the electrode confirmation is generated is indicated in gray color.

In a comparative example in which the electrode confirmation prevention process is not performed, the electrode confirmation occurs in the electrode confirmation alarm signal at each timing when the waveform is clipped to the upper limit value in the electrocardiogram. Therefore, electrode confirmation is generated in response to frequent clipping, and the generated electrode confirmation highly probably include electrode confirmation that does not need to be handled.

In the embodiment in which the electrode confirmation prevention process is performed, the alarm delay process is performed, and the electrode confirmation is started in the electrode confirmation alarm signal when the frequency of the electrode confirmation in the electrode confirmation message signal becomes the first threshold or more or when the period in which the measurement value is invalid calculated based on the HR output value becomes the second threshold or more. Further, the electrode confirmation is ended in the electrode confirmation alarm signal when the period in which the measurement value is valid calculated based on the HR output value becomes the third threshold or more. Accordingly, the electrode confirmation can be appropriately notified while reducing electrode confirmation that does not need to be handled.

(Central Monitor 100)

Figure 9:
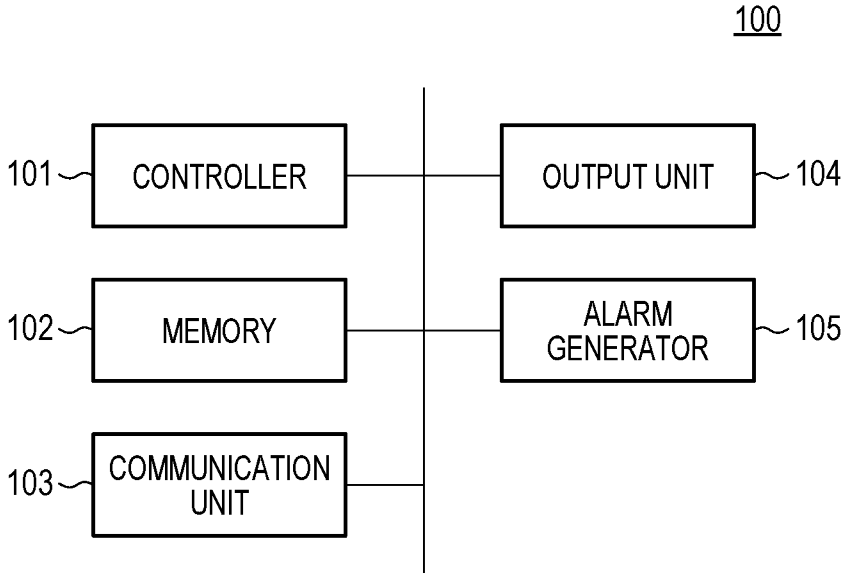
FIG. 9 is a block diagram of a hardware configuration of a central monitor.

FIG. 9 is a block diagram of a hardware configuration of the central monitor 100. The central monitor 100 may include a controller 101, a memory 102, a communication unit 103, an output unit 104, and an alarm generator 105. These components are mutually connected via a bus. Among these component elements of the central monitor 100, the basic configurations of component elements corresponding to the component elements of the bed-side monitor 110 is the same as or similar to the basic configurations of the bed-side monitor 110, and thus the redundant description thereof is omitted.

The controller 101 receives physiological alarm signals such as an electrocardiogram and an irregular pulse and electrode confirmation alarm signals, which are device alarm signals, from each bed-side monitor 110 by the communication unit 103.

The memory 102 stores the electrocardiogram, the physiological alarm signal, and the electrode confirmation alarm signal in association with the time. The electrocardiogram, the physiological alarm signal, and the electrode confirmation alarm signal may be stored in association with the identification information.

The output unit 104 displays (outputs) the electrocardiogram, the occurrence of the physiological alarm in the physiological alarm signal, and the occurrence of the electrode confirmation in the electrode confirmation alarm signal. The output unit 104 may include an amplifier and a speaker to output the alarms in an audibly recognizable manner. The output unit 104 may transmit (output) to another apparatus as data the electrocardiogram, the generation of the physiological alarm in the physiological alarm signal, and the occurrence of the electrode confirmation in the electrode confirmation alarm signal. The output unit 104 may be configured with a printer to output the electrocardiogram, the occurrence of the physiological alarm in the physiological alarm signal, and the occurrence of the electrode confirmation in the electrode confirmation alarm signal by forming an image on a sheet.

The alarm generator 105 notifies the generation of the physiological alarm included in the physiological alarm signal by outputting voice, light, image, or the like. The alarm generator 105 notifies the generation of the electrode confirmation included in the electrode confirmation alarm signal by outputting sound, light, image, vibration, indicator, or the like. The alarm generator 105 may output the alarms for each type of alarm in a manner recognizable by the difference in, for example, tone, color of light, images, or the like.

Figure 10:
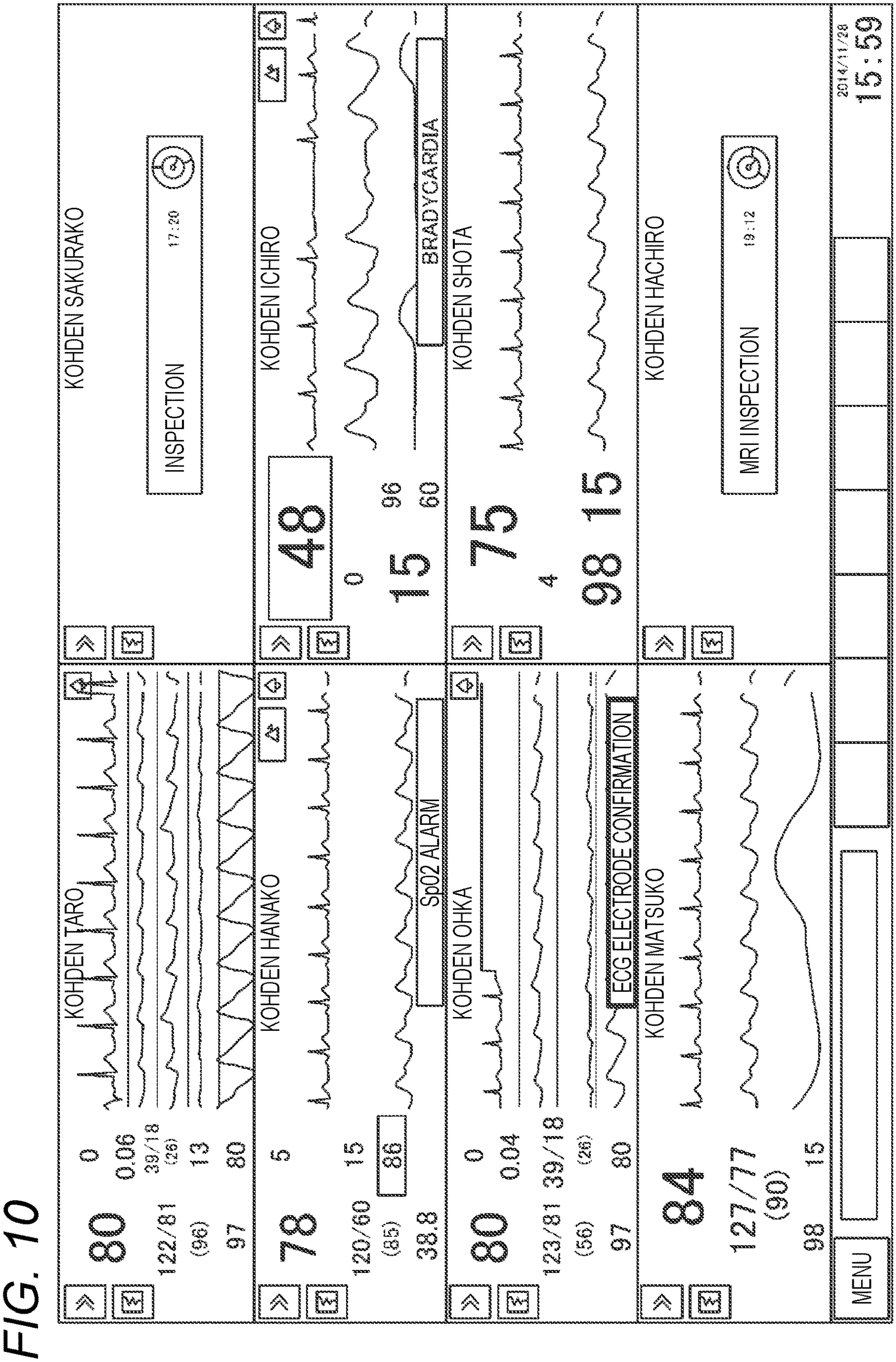
FIG. 10 illustrates a display screen of physiological information and various alarms.

FIG. 10 illustrates a display screen of the physiological information and the various alarms displayed on the output unit 104.

In the example of FIG. 10, the physiological information and the occurrence of various alarms are displayed by the name of the patient or the like. As the physiological information, an electrocardiogram, the heart rate, the blood pressure, the SpO2, and the like are displayed. The occurrence of an SpO2 alarm, which is a physiological alarm, is displayed for a patient named "Kohden Hanako". The occurrence of electrode confirmation, which is a device alarm, is displayed for a patient named "Kohden Ohka".

In the present embodiment, the generation of the electrode confirmation alarm signal and the generation of the physiological alarm signal may be performed independently. However, the electrode confirmation alarm signal and the physiological alarm signal may be generated using the same input signal. Accordingly, the physiological alarm in the physiological alarm signal can be generated even during the period in which the electrode confirmation is generated in the electrode confirmation alarm signal. That is, for example, irregular pulse can be detected based on the electrocardiogram simultaneously when electrode confirmation is generated in the electrode confirmation alarm signal, and electrode confirmation in the electrode confirmation alarm signal and a physiological alarm of irregular pulse in the physiological alarm signal can be generated as follows when irregular pulse is detected. Examples include: (1) simultaneously generate electrode confirmation and a physiological alarm; (2) prioritizing a physiological alarm rather than electrode confirmation; and (3) prioritizing electrode confirmation rather than a physiological alarm.

The operation of the medical system 10 will be described.

Figure 11:
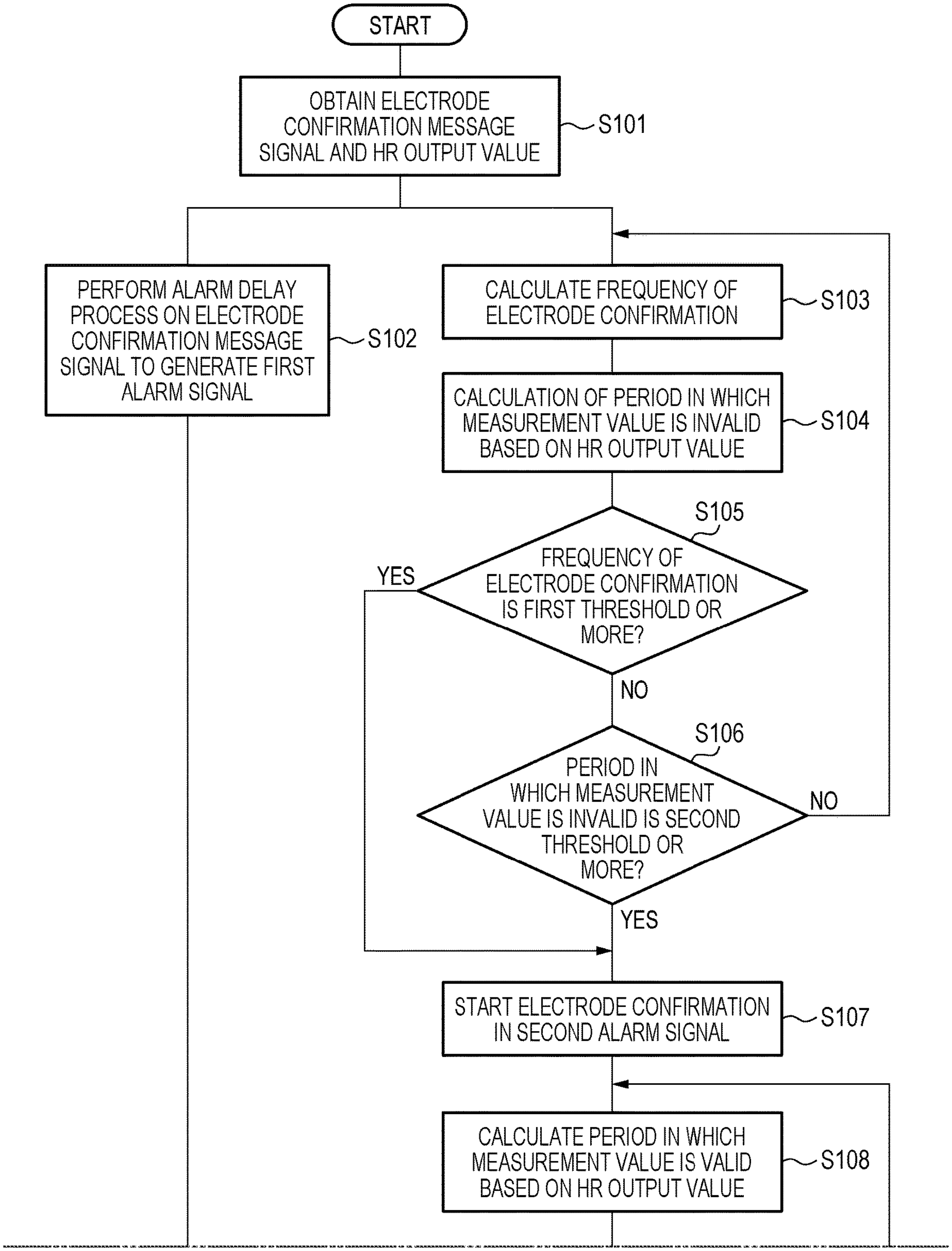
FIG. 11 is a flowchart illustrating the operation of the medical system.

FIG. 11 is a flowchart illustrating the operation of the medical system 10. This flowchart can be executed by the electrode confirmation prevention processor 117 of the bed-side monitor 110 according to a program.

The electrode confirmation prevention processor 117 obtains the electrode confirmation message signal and the HR output value from the ECG analysis processor 116 (S101).

The electrode confirmation prevention processor 117 performs the alarm delay process on the electrode confirmation message signal to generate a first alarm signal (S102). The first alarm signal is merged with the second alarm signal generated in the step described below in each period of time, and then transmitted (output) to the central monitor 100 as the electrode confirmation alarm signal.

The electrode confirmation prevention processor 117 calculates the frequency of electrode confirmation based on the electrode confirmation message signal (S103).

The electrode confirmation prevention processor 117 calculates the period in which the measurement value is invalid based on the HR output value (S104).

The electrode confirmation prevention processor 117 determines whether the frequency of electrode confirmation is the first threshold or more (S105). If it is determined that the frequency of electrode confirmation is the first threshold or more (S105: YES), the electrode confirmation prevention processor 117 starts electrode confirmation in the generated second alarm signal (S107).

If it is determined that the frequency of electrode confirmation is not the first threshold or more (S105: NO), the electrode confirmation prevention processor 117 determines whether the period in which the measurement value is invalid is the second threshold or more (S106). If it is determined that the period in which the measurement value is invalid is not the second threshold or more (S106: NO), the electrode confirmation prevention processor 117 returns to step S103 and continues the processing.

If the electrode confirmation prevention processor 117 determines that the period in which the measurement value is invalid is the second threshold or more (S106: YES), the electrode confirmation prevention processor 117 starts electrode confirmation in the second alarm signal (S107).

The electrode confirmation prevention processor 117 calculates the period in which the measurement value is valid based on the HR output value (S108).

The electrode confirmation prevention processor 117 determines whether the period in which the measurement value is valid is the third threshold or more (S109). If the electrode confirmation prevention processor 117 determines that the period in which the measurement value is valid is not the third threshold or more (S109: NO), the electrode confirmation prevention processor 117 returns to step S108 and continues the processing.

If the electrode confirmation prevention processor 117 determines that the period in which the measurement value is valid is the third threshold or more (S109: YES), the electrode confirmation prevention processor 117 ends the electrode confirmation in the second alarm signal (S110).

Modification 1

Figure 12:
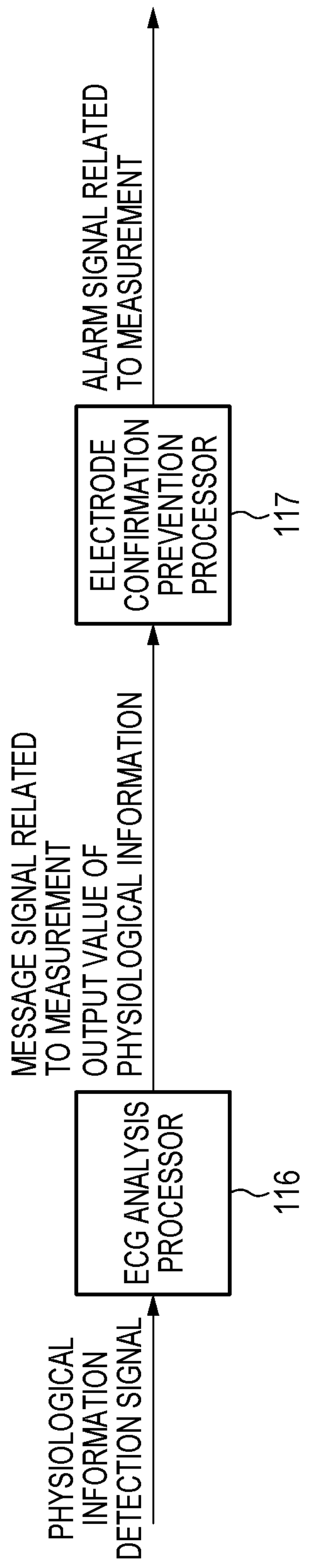
FIG. 12 is a block diagram for explaining the functions of an ECG analysis processor and an electrode confirmation prevention processor according to a modification of the embodiment.

FIG. 12 is a block diagram for explaining the functions of an ECG analysis processor 116 and an electrode confirmation prevention processor 117 according to a modification of the embodiment.

The embodiment described above has described an example in which the detection signal of the physiological information detected by the sensor 114 is an electrocardiogram.

However, the detection signal of the physiological information detected by the sensor 114 may be the arterial blood oxygen saturation, the blood pressure, the respiration, carbon dioxide (CO2) of expiration and inhalation, the ST value, the VPC rate, the pulse rate, the CCO value, a score (indicating the condition of the patient), and the like.

The ECG analysis processor 116 analyzes the detection signal of the physiological information to calculate the message signal related to the measurement of the physiological information and the output value of the physiological information. The ECG analysis processor 116 may calculate a plurality of message signals related to the measurement of physiological information. The ECG analysis processor 116 may calculate a plurality of output values of the physiological information. The message signal related to the measurement of the physiological information may include a signal of any message related to the measurement of the physiological information. The message signal related to the measurement of the physiological information may be a message signal indicating whether "radio wave interruption" has occurred or a message signal indicating whether "probe confirmation" has occurred. Alternatively, the message signal related to the measurement of the physiological information may be a message signal indicating whether electromagnetic interference has occurred, whether occlusion of a line or a flow has occurred, or whether device failure has occurred. The output value of the physiological information may be an output value of the QT time, an output value of the R-R time, an output value of the P-P time, an output value of the blood pressure, or the like.

The electrode confirmation prevention processor 117 generates and outputs a measurement-related alarm signal based on at least one of the message signal related to the measurement of the physiological information or the output value of the physiological information. The electrode confirmation prevention processor 117 may generate and output the measurement-related alarm signal based on a plurality of message signals related to the measurement of the physiological information and a plurality of output values of the physiological information. The measurement-related alarm signal may include all the alarm signals related to the measurement of the physiological information. The measurement-related alarm signal is not limited to the electrode confirmation alarm signal, and may be a signal for notifying an alarm of "radio wave interruption" or a signal for notifying an alarm of "probe confirmation". Alternatively, the measurement-related alarm signal may be a signal for notifying an alarm of electromagnetic interference, a signal for notifying an alarm of occlusion of a line or a flow, or a signal for notifying an alarm of device failure.

Modification 2

The bed-side monitor 110 may further include a switching unit for switching between a first mode and a second mode. The first mode is for outputting a message signal related to the measurement of the physiological information in place of the electrode confirmation alarm signal. The second mode is for outputting an electrode confirmation alarm signal (that is, an integrated alarm signal obtained by merging the first alarm signal and the second alarm signal). The switching unit may be configured with the controller 111. For example, the controller 111 may receive a switching control signal based on a switching input by the user to a user terminal (not illustrated) from the user terminal by the communication unit 113, and switch between the first mode and the second mode based on the switching control signal.

Modification 3

Figure 13:
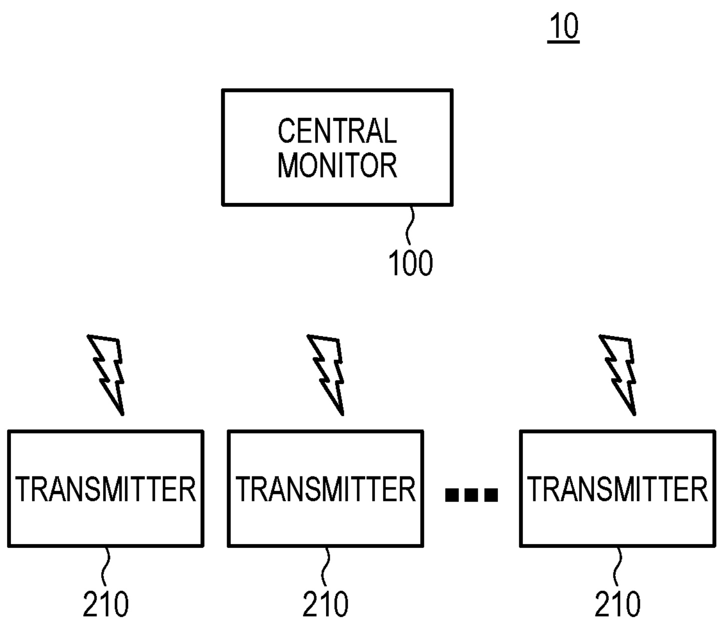
FIG. 13 is a schematic configuration diagram of a modification of the medical system.
Figure 14:
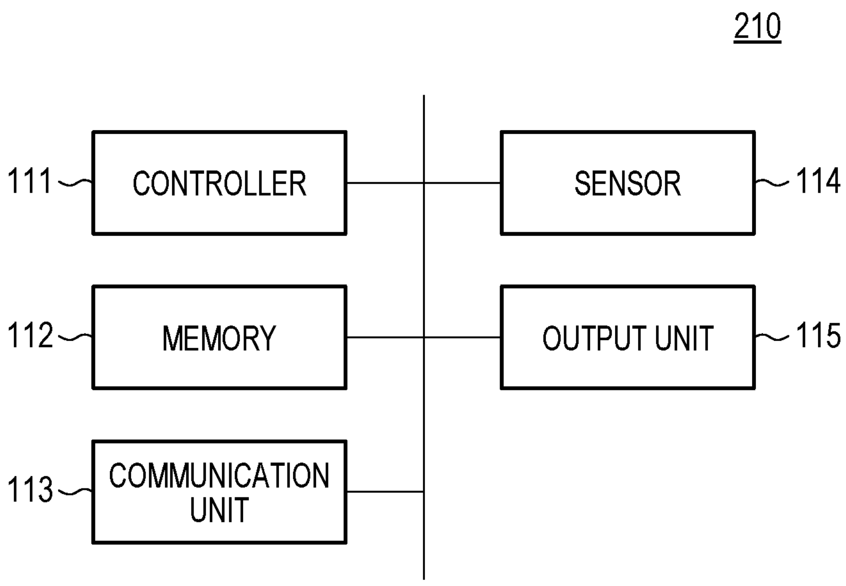
FIG. 14 is a block diagram of a hardware configuration of a transmitter.
Figure 15:
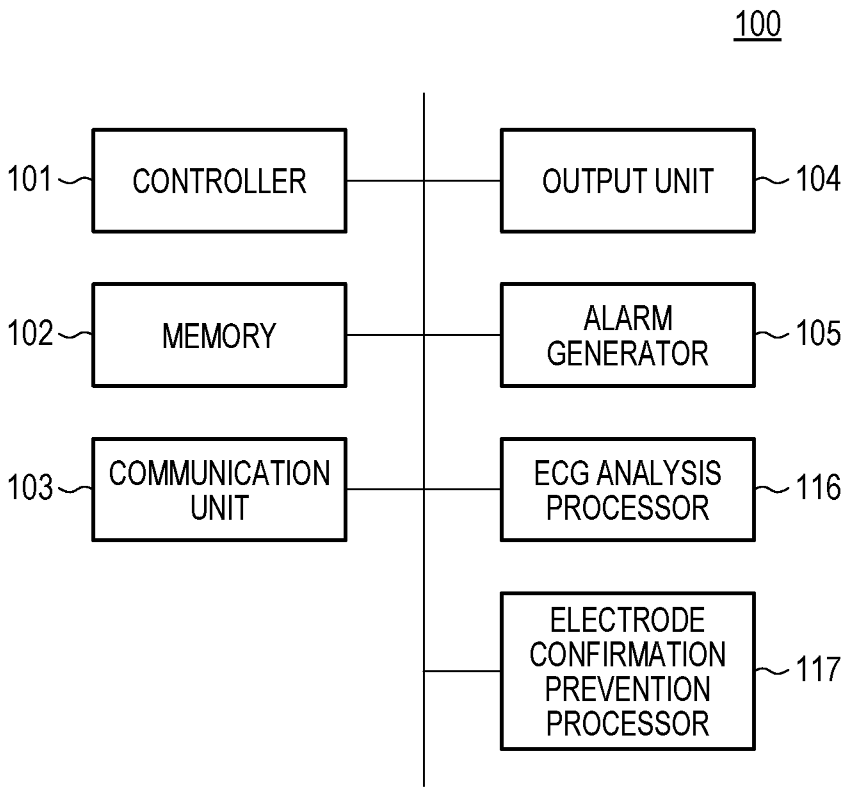
FIG. 15 is a block diagram of a hardware configuration of a central monitor.

FIG. 13 is a schematic configuration diagram of Modification 3 of the medical system 10. FIG. 14 is a block diagram of a hardware configuration of a transmitter 210. FIG. 15 is a block diagram of a hardware configuration of the central monitor 100. As illustrated in FIG. 13, the medical system 10 may include the central monitor 100 and the transmitter 210. In this modification, the transmitter 210 may include a controller 111, a memory 112, a communication unit 113, a sensor 114, and an output unit 115. The central monitor 100 may include a controller 101, a memory 102, a communication unit 103, an output unit 104, an alarm generator 105, an ECG analysis processor 116, and an electrode confirmation prevention processor 117. In FIGS. 14 and 15, components denoted by the same reference numerals as those in FIGS. 2 and 9 referred to in the description of the above-described embodiment basically have the same configuration and function, and thus redundant description thereof will be omitted.

In the present modification, the ECG analysis processor 116 and the electrode confirmation prevention processor 117 is not included in the transmitter 210 but is included in the central monitor 100. Accordingly, a detection signal of physiological information is transmitted from each transmitter 210 to the central monitor 100 by the communication unit 113 through wireless communication. The ECG analysis processor 116 included in the central monitor 100 analyzes the received detection signal to calculate the message signal related to the measurement of the physiological information and the output value of the physiological information. The electrode confirmation prevention processor 117 included in the central monitor 100 generates and outputs a device alarm signal based on at least one of the message signal related to the measurement of the physiological information or the output value of the physiological information. The device alarm signal may include an electrode confirmation alarm signal (see FIG. 3). The abnormality notified by the device alarm signal may include, for example, an abnormality of an apparatus or the like including a measurement device (device or element) constituting the sensor 114, an abnormality of the attachment state such as detachment of the sensor 114 attached to the patient, and an abnormality of the measurement environment such as radio wave interruption or mixed noise. Specifically, examples of the device alarm may include "electrode confirmation", "radio wave interruption", and "probe confirmation". "Radio wave interruption" is an alarm indicating that the reception state of radio waves is bad, interference occurs, information cannot be received, or the like.

The embodiment has the following effects.

The first alarm signal and the second alarm signal are output after generating the second alarm signal based on at least one of the first alarm signal generated based on the message signal related to the measurement of the physiological information or the period in which the measurement value of the physiological information is invalid calculated based on the output value of the physiological information. Accordingly, alarms can be appropriately notified while reducing the number of alarms that do not need to be handled.

The second alarm signal generator starts an alarm in the second alarm signal if at least one of a first condition or a second condition is satisfied, and does not start the alarm in the second alarm signal if neither the first condition nor the second condition is satisfied, the first condition being an occurrence frequency of the message signal related to the measurement being a predetermined first threshold or more, and the second condition being the period in which the measurement value is invalid being a predetermined second threshold or more. Accordingly, it is possible to easily and appropriately notify alarms that highly probably need to be handled while reducing the alarms that do not need to be handled.

When an alarm is started in the second alarm signal, the alarm in the second alarm signal is continued until a period in which the measurement value is valid continues for a predetermined third threshold or more. Accordingly, it is possible to call attention to an alarm if the alarm continues for a relatively long time and thus needs to be handled, while appropriately reducing the occurrence of alarms.

After the alarm is started in the second alarm signal, the alarm in the second alarm signal is ended if the period in which the measurement value is valid continues for the third threshold or more. Accordingly, it is possible to call attention to an alarm by the alarm continuing for an appropriate time, while appropriately reducing the occurrence of alarms.

The message signal related to the measurement is a message signal of sensor confirmation related to attachment of a sensor for measuring the physiological information to a measurement subject. As a result, it is possible to simply and more appropriately notify a message of sensor confirmation that highly probably needs to be handled, while reducing messages of sensor confirmation that do not need to be handled.

With respect to the message signal of the sensor confirmation, the first alarm signal is generated by masking the sensor confirmation for a predetermined time from occurrence of the sensor confirmation. Accordingly, it is possible to appropriately reduce electrode confirmation that does not need to be performed.

Control is performed to output the first alarm signal and the second alarm signal as an integrated alarm signal obtained by merging the first alarm signal and the second alarm signal. Accordingly, it is possible to perform appropriate alarm notification such that the number of types of alarms to be notified is reduced while reducing the number of alarms that do not need to be handled.

A switching unit, which is configured to switch between a first mode for outputting a message signal related to the measurement and a second mode for outputting the integrated alarm signal, performs control to output the message signal related to the measurement when the switching unit switches to the first mode, and performs control to output the integrated alarm signal when the switching unit switches to the second mode. Accordingly, it is possible to perform appropriate alarm notification flexibly according to the intention of the user, while reducing the alarms that do not need to be handled.

The physiological information is a heart rate, an electrocardiogram, an SpO2, a respiratory rate, an ST value, a VPC rate, a pulse rate, a CCO value, or a score indicating a condition of a measurement subject. Accordingly, in the measurement of the physiological information, it is possible to expand the range of the physiological information in which the alarm notification can be performed appropriately, while reducing the alarms that do not need to be handled.

The first alarm signal and the second alarm signal are alarm signals of electrode confirmation. Accordingly, it is possible to more easily and appropriately notify electrode confirmation that highly probably needs to be handled, while reducing electrode confirmation that does not need to be handled.

The message signal related to the measurement is a message signal of electrode confirmation, and the output value of the physiological information is an output value of a heart rate. Accordingly, it is possible to more easily and appropriately notify electrode confirmation that highly probably needs to be handled, while reducing electrode confirmation that does not need to be handled.

Although the embodiment of the presently disclosed subject matter has been described in detail, the presently disclosed subject matter is not limited to the embodiment described above.

For example, some or all of the functions and configurations of the bed-side monitor 110 may be included in the functions and configurations of the central monitor 100. Some or all of the functions and configurations of the central monitor 100 may be included in the functions and configurations of the bed-side monitor 110. For example, the bed-side monitor 110 may also include an element corresponding to the alarm generator 105 included in the central monitor 100.

For example, some or all of the functions achieved by the program in the embodiment described above may be achieved by hardware such as a circuit.

In the flowchart described above, a part of the steps may be omitted, and other steps may be added. In addition, a part of each step may be executed simultaneously, and one step may be divided into a plurality of steps and executed.

What is claimed is:

1. An alarm control system comprising:

one or more processors collectively configured to obtain a message signal related to measurement of physiological information and an output value of the physiological information;

a first alarm signal generator configured to generate a first alarm signal based on the message signal related to the measurement;

a second alarm signal generator configured to generate a second alarm signal based on at least one of the message signal related to the measurement or a period in which a measurement value is invalid, the period being calculated based on the output value of the physiological information; and an output controller configured to perform control to output the first alarm signal and the second alarm signal.

2. The alarm control system according to claim 1, wherein the second alarm signal generator starts an alarm in the second alarm signal if at least one of a first condition or a second condition is satisfied, and does not start the alarm in the second alarm signal if neither the first condition nor the second condition is satisfied, the first condition being an occurrence frequency of the message signal related to the measurement being a predetermined first threshold or more, and the second condition being the period in which the measurement value is invalid being a predetermined second threshold or more.

3. The alarm control system according to claim 1, wherein when the second alarm signal generator starts an alarm in the second alarm signal, the second alarm signal generator continues the alarm in the second alarm signal until a period in which the measurement value is valid continues for a predetermined third threshold or more, the period being a period other than the period in which the measurement value is invalid.

4. The alarm control system according to claim 3, wherein after the second alarm signal generator starts the alarm in the second alarm signal, the second alarm signal generator ends the alarm in the second alarm signal if the period in which the measurement value is valid continues for the third threshold or more.

5. The alarm control system according to claim 1, wherein the message signal related to the measurement is a message signal of sensor confirmation related to attachment of a sensor for measuring the physiological information to a measurement subject.

6. The alarm control system according to claim 5, wherein with respect to the message signal of the sensor confirmation, the first alarm signal generator generates the first alarm signal by masking the sensor confirmation for a predetermined time from occurrence of the sensor confirmation.

7. The alarm control system according to claim 1, wherein the output controller performs control to output the first alarm signal and the second alarm signal as an integrated alarm signal obtained by merging the first alarm signal and the second alarm signal.

8. The alarm control system according to claim 7, wherein the one or more processors are further collectively configured to switch between a first mode for outputting a message signal related to the measurement and a second mode for outputting the integrated alarm signal, and wherein the output controller performs control to output the message signal related to the measurement when one or more processors switch to the first mode, and performs control to output the integrated alarm signal when the one or more processors switch to the second mode.

9. The alarm control system according to claim 1, wherein the physiological information is a heart rate, an electrocardiogram, an SpO2, a respiratory rate, an ST value, a VPC rate, a pulse rate, a CCO value, or a score indicating a condition of a measurement subject.

10. The alarm control system according to claim 5, wherein the first alarm signal and the second alarm signal are alarm signals of electrode confirmation.

11. The alarm control system according to claim 1, wherein the message signal related to the measurement is a message signal of electrode confirmation, and the output value of the physiological information is an output value of a heart rate.

12. An alarm control method executed by an alarm control system, the alarm control method comprising:| obtaining a message signal related to measurement of physiological information and an output value of the physiological information;

generating a first alarm signal based on the message signal related to the measurement;

generating a second alarm signal based on at least one of the message signal related to the measurement or a period in which a measurement value is invalid, the period being calculated based on the output value of the physiological information; and performing control to output the first alarm signal and the second alarm signal.

13. A non-transitory computer-readable storage medium storing an alarm control program for causing a computer to execute:

obtaining a message signal related to measurement of physiological information and an output value of the physiological information;

generating a first alarm signal based on the message signal related to the measurement;

generating a second alarm signal based on at least one of the message signal related to the measurement or a period in which a measurement value is invalid, the period being calculated based on the output value of the physiological information; and performing control to output the first alarm signal and the second alarm signal.

14. The alarm control method according to claim 12, further comprising:

starting an alarm in the second alarm signal if at least one of a first condition or a second condition is satisfied, and not starting the alarm in the second alarm signal if neither the first condition nor the second condition is satisfied, the first condition being an occurrence frequency of the message signal related to the measurement being a predetermined first threshold or more, and the second condition being the period in which the measurement value is invalid being a predetermined second threshold or more.

15. The non-transitory computer-readable storage medium according to claim 13, further causing the computer to execute:

starting an alarm in the second alarm signal if at least one of a first condition or a second condition is satisfied, and not starting the alarm in the second alarm signal if neither the first condition nor the second condition is satisfied, the first condition being an occurrence frequency of the message signal related to the measurement being a predetermined first threshold or more, and the second condition being the period in which the measurement value is invalid being a predetermined second threshold or more.

16. The alarm control method according to claim 12, wherein when an alarm in the second alarm signal is started, the alarm continues in the second alarm signal until a period in which the measurement value is valid continues for a predetermined third threshold or more, the period being a period other than the period in which the measurement value is invalid.

17. The non-transitory computer-readable storage medium according to claim 13, wherein when an alarm in the second alarm signal is started, the alarm continues in the second alarm signal until a period in which the measurement value is valid continues for a predetermined third threshold or more, the period being a period other than the period in which the measurement value is invalid.

18. The alarm control method according to claim 12, wherein the message signal related to the measurement is a message signal of sensor confirmation related to attachment of a sensor for measuring the physiological information to a measurement subject.

19. The non-transitory computer-readable storage medium according to claim 13, wherein the message signal related to the measurement is a message signal of sensor confirmation related to attachment of a sensor for measuring the physiological information to a measurement subject.

20. The alarm control system method to claim 12, further comprising:

outputting the first alarm signal and the second alarm signal as an integrated alarm signal obtained by merging the first alarm signal and the second alarm signal.

21. The non-transitory computer-readable storage medium according to claim 13, further causing the computer to execute:

outputting the first alarm signal and the second alarm signal as an integrated alarm signal obtained by merging the first alarm signal and the second alarm signal.

* * * * *